US010555983B2

(12) United States Patent
Shin et al.

(10) Patent No.: US 10,555,983 B2
(45) Date of Patent: Feb. 11, 2020

(54) COMPOSITION FOR BRAIN ACTIVATION, COMPRISING GINSENG FRUIT EXTRACT

(71) Applicant: AMOREPACIFIC CORPORATION, Seoul (KR)

(72) Inventors: Hyun Jung Shin, Yongin-si (KR); Chan Woong Park, Yongin-si (KR); Su Hwan Kim, Yongin-si (KR); Dae Bang Seo, Yongin-si (KR); Wan Gi Kim, Yongin-si (KR); Sang Jun Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 436 days.

(21) Appl. No.: 14/781,146

(22) PCT Filed: Mar. 27, 2014

(86) PCT No.: PCT/KR2014/002612
§ 371 (c)(1),
(2) Date: Sep. 29, 2015

(87) PCT Pub. No.: WO2014/163328
PCT Pub. Date: Oct. 9, 2014

(65) Prior Publication Data
US 2016/0051605 A1    Feb. 25, 2016

(30) Foreign Application Priority Data

Apr. 2, 2013  (KR) .................. 10-2013-0035600
Mar. 24, 2014  (KR) .................. 10-2014-0033892

(51) Int. Cl.
| A61K 36/258 | (2006.01) |
| A61K 31/704 | (2006.01) |
| A23L 33/105 | (2016.01) |
| A23L 2/52 | (2006.01) |

(52) U.S. Cl.
CPC .............. *A61K 36/258* (2013.01); *A23L 2/52* (2013.01); *A23L 33/105* (2016.08); *A61K 31/704* (2013.01); *A23V 2002/00* (2013.01)

(58) Field of Classification Search
CPC ........ A23V 2200/322; A23V 2250/156; A23V 2250/21; A23V 2250/702; A23V 2250/704; A23V 2250/712; A23L 2/52; A23L 33/105; A23L 1/3002; A61K 36/258; A61K 31/704
See application file for complete search history.

(56) References Cited

U.S. PATENT DOCUMENTS

| 6,083,932 A | 7/2000 | Pang et al. |
| 8,877,264 B2 | 11/2014 | Park et al. |
| 2014/0248380 A1 | 9/2014 | Park et al. |

FOREIGN PATENT DOCUMENTS

| CN | 1689620 A | * | 11/2005 |
| CN | 101720225 A | | 6/2010 |
| CN | 101966292 A | | 2/2011 |
| EP | 1213026 A1 | | 6/2002 |
| JP | 2010-528109 A | | 8/2010 |
| KR | 10-2006-0039766 A | | 5/2006 |
| KR | 10-2008-0114286 A | | 12/2008 |
| KR | 10-2011-0078524 A | | 7/2011 |
| KR | 10-2011-0079564 A | | 7/2011 |
| WO | 92/22307 A1 | | 12/1992 |
| WO | 99/30725 A1 | | 6/1999 |
| WO | 2013/109051 A1 | | 7/2013 |

OTHER PUBLICATIONS

Vicony Teas "Vicony Teas Directory:Ginseng Tea" <URL:http://www.viconyteas.com/directory/tea-encyclopedia/ginseng-tea.html>, Jun. 10, 2011 (archived Sep. 11, 2011), 2 pages.*
Kim, J-H "Cardiovascular Diseases and Panax ginseng: A Review on Molecular Mechanisms and Medical Applications" J Ginseng Res. Jan. 2012; 36(1): 16-26; doi: 10.5142/jgr.2012.36.1.16. (Year: 2012).*
International Search Report for International Application. No. PCT/KR2014/002612, dated Jul. 17, 2014, 7 pages (and English Translation, 11 pages).
Jung, "Studies on the effects of ginseng: regeneration of hippocampal nervous system and cognitive enhancement," Ajou University, (2004) , 37 pages.
Jung, et al.: "Chronic Fatigue Syndrome," *Yeungnam University Journal of Medicine*, 24(1):1-10 (Jun. 2007).
Extended European Search Report from European Application No. 14779685.8, dated Dec. 7, 2016, 8 pages.
Database WPI Week 200946 Thomson Scientific, London, GB; AN 2009-F19770 XP002764704, & KR 2008 0114286 A (Yong J P), Dec. 31, 2008, 2 pages.
Database WPI Week 199302 Thomson Scientific, London, GB; AN 1993-017895 XP002764705, & WO 92/22307 AI (Kanebo Ltd), Dec. 23, 1992, 2 pages.
Database WPI Week 201220 Thomson Scientific, London, GB; AN 2012-B52064 XP002764706, & KR 2011 0078524 A (Amorepacific Corp), Jul. 7, 2011, 2 pages.
See et al., "In vitro effects of echinacea and ginseng on natural killer and antibody-dependent cell cytotoxicity in healthy subjects and chronic fatigue syndrom or acquired immunodeficiency syndrom patients," Immunopharmacology 35:229-235 (1997).

(Continued)

*Primary Examiner* — Aaron J Kosar
(74) *Attorney, Agent, or Firm* — Merchant & Gould P.C.

(57) ABSTRACT

Provided in the present specification is a composition for brain activation, comprising ginseng fruit extract as an active ingredient. The composition according to the present specification allows an increase in blood flow in the brain and thus has an effect of ameliorating chronic fatigue syndrome. In addition, the composition according to the present specification activates the brain, and as a result, strengthens connectivity strength between the frontal lobe and the occipital lobe and thus has an effect of improving problem-solving accuracy and reducing solving time in the area of cognitive ability. Therefore, the composition according to the present specification can be used as a pharmaceutical composition or a food composition for patients suffering from chronic fatigue syndrome.

6 Claims, 7 Drawing Sheets

(56) References Cited

OTHER PUBLICATIONS

Wang et al., "Improvement of Memory in Mice and Increase of Hippocampal Excitability in Rats by Ginsenoside Rg1's Metabolites Ginsenoside RH1 and Protopanaxatriol," Journal of Pharmacological Sciences, 109:504-510 (2009).
Vogler et al., "The efficacy of ginseng. A systematic review of randomised clinical trials," Eur J. Clin. Pharmacol, 55:567-575 (1999).
Office Action from Japanese Patent Application No. 2016-506227 dated Dec. 19, 2017.
Gao Yimin, Chemical Industry Press, vol. 1, May 2004, pp. 267-269.
Office Action for Chinese Patent Application No. 201410132265.7, dated Aug. 2, 2018.
All about Korean Ginseng, Korean Society of Ginseng, Dec. 12, 2008, 112 pages.
Office Action from Japanese Application No. 2016-506227, dated May 21, 2019, 12 pages.

* cited by examiner

COMPOSITION FOR BRAIN ACTIVATION, COMPRISING GINSENG FRUIT EXTRACT

This application is a U.S. National Stage Application under 35 U.S.C. § 371 of International Patent Application No. PCT/KR2014/002612 filed 27 Mar. 2014, which claims the benefit of priority to Korean Patent Application No. 10-2013-0035600 filed 2 Apr. 2013 and to Korean Patent Application No. 10-2014-0033892 filed 24 Mar. 2014, the disclosures of all of which are hereby incorporated by reference in their entireties. The International Application was published in Korean on 9 Oct. 2014 as WO 2014/163328.

TECHNICAL FIELD

The present disclosure relates to a composition for activating the brain, more particularly to a composition containing a ginseng fruit extract, which exhibits superior effective of improving brain activation.

BACKGROUND ART

Human gets all information about the situations inside and outside his/her body through sensation and perception. The human brain has a region where the brain cells specially trained to perform the cognitive function. When the region is locally damaged, disorder occurs for each cognitive function.

The disorder of the cognitive function may occur due to various causes. Examples of the cognitive function disorder include cognitive function disorders caused by degenerative brain diseases including dementia, Parkinson's disease, stroke, Huntington's disease, etc., alcoholic cognitive function disorder, aging-induced cognitive function disorder, loss of brain function due to accidents, cognitive function disorder caused by cerebral hemorrhage, attention deficit hyperactivity disorder (ADHD), schizophrenia, and cognitive function disorder caused by chronic fatigue syndrome. Dementia, which is a representative degenerative brain disease, is a brain disease showing disorder of the overall cognitive function. It is usually caused by chronic or progressive brain diseases and exhibits a number of the so-called higher cerebral functions such as memory, thought, understanding, calculation, learning, language, judgment, etc. Also, as a degenerative change with aging, the brain function declines gradually, and as a result, cognitive ability declines.

Chronic fatigue syndrome (CFS) refers to prolonged severe fatigue with no known cause for at least 6 months and is commonly found in modern people. The chronic fatigue syndrome is characterized by severe fatigue which is not substantially rest and makes the patient very weak (United States Centers for Disease Control and Prevention, Fukuda et al. 1994).

The criteria for chronic fatigue syndrome include, together with fatigue, four or more of impaired memory or concentration, sore throat, tender lymph nodes, muscle pain, arthralgia, headaches of a new kind, unrefreshing sleep, post-exertional malaise, etc. And, symptoms commonly accompanied by the chronic fatigue syndrome include cognitive function decline such as concentration deficit, attention deficit and memory deficit. These symptoms suggest that chronic fatigue syndrome is accompanied by the disorder of the central nervous system. In addition, patients with chronic fatigue syndrome show signs of decreased brain blood flow in single-photon emission computed tomography (SPECT) more frequently than normal people or patients with depression.

Although no consistent results are reported on the neuropsychological examination of the cognitive function in chronic fatigue syndrome, recent studies show that the patients with chronic fatigue syndrome show significant decline in working memory and information processing.

The exact cause of chronic fatigue syndrome exhibiting such symptoms is not known and no medication is known that can permanently relieve the symptoms. In addition, many of the currently used drugs have mild adverse effects such as weariness, dizziness and nausea and severe adverse effects such as addiction and liver damage.

Therefore, development of a medicine that can treat cognitive function disorder and chronic fatigue syndrome without adverse effects is necessary. Because patients with chronic fatigue syndrome show signs of decreased brain blood flow in SPECT more frequently than normal people or patients with depression, if brain activity can be enhanced by increasing brain blood flow, it will be effective in treating chronic fatigue syndrome and improving accompanying symptoms.

DISCLOSURE

Technical Problem

The inventors of the present disclosure have researched using ginseng fruit, which is an aerial part of ginseng, to improve chronic fatigue syndrome or cognitive function disorder. In doing so, they have identified that an extract of ginseng fruit which is different from ginseng root in ingredients and composition is effective in improving chronic fatigue syndrome and cognitive function and have completed the present disclosure.

The present disclosure is directed to providing a composition for activating the brain, for improving, treating or preventing chronic fatigue syndrome or for improving cognitive ability, which contains a ginseng fruit extract.

Technical Solution

In an aspect, the present disclosure provides a composition for activating the brain, for improving chronic fatigue syndrome or for improving cognitive ability, which contains a ginseng fruit extract as an active ingredient.

Advantageous Effects

A composition according to an exemplary embodiment of the present disclosure is effective in reducing chronic fatigue and depression and improving problem-solving accuracy and reducing problem-solving time in the area of cognitive ability by facilitating brain blood flow and thereby activating the brain.

Also, it enables effective information processing by increasing overall brain blood flow and thereby promoting brain activation.

As a result, it improves the ability to respond to or cope with stresses or stimuli, thereby reducing mental and physical fatigue in daily lives and increasing resistance to stresses.

BEST MODE

Korean Patent Application No. 10-2013-0035600, which was filed on Apr. 2, 2013 and Korean Patent Application No. 10-2014-0033892, which was filed on Mar. 24, 2014 are incorporated herein in its entirety for all purposes. In addition, this application claims the priority of Korean Patent Application No. 10-2013-0035600 and Korean Patent Application No. 10-2014-0033892 and all the benefits accruing therefrom, the contents of which in its entirety are herein incorporated by reference.

In an aspect, the present disclosure may relate to a composition for activating the brain, which contains a ginseng fruit extract as an active ingredient. Specifically, the composition for activating the brain may be a pharmaceutical or food composition for activating the brain.

In an aspect, the present disclosure may relate to a method for activating the brain, which includes administering a ginseng fruit extract to a subject in need of brain activation.

In an aspect, the present disclosure may relate to a use of a ginseng fruit extract for activating the brain.

In an aspect, the present disclosure may relate to a ginseng fruit extract for use in activating the brain.

In an aspect, the present disclosure may relate to a composition for improving cognitive function, which contains a ginseng fruit extract as an active ingredient. Specifically, the composition for improving cognitive function may be a pharmaceutical or food composition.

In an aspect of the present disclosure, the improvement of cognitive function may mean improvement of cognitive function disorders caused by various diseases, aging, accidents, etc. Specifically, the diseases may include degenerative brain diseases including dementia, Parkinson's disease, stroke, Huntington's disease, etc., although not being limited thereto. Also, in an aspect of the present disclosure, the cognitive function disorder may include alcoholic cognitive function disorder, cognitive function disorder caused by cerebral hemorrhage, loss of brain function due to accidents, aging-induced cognitive function disorder, schizophrenia, attention deficit hyperactivity disorder (ADHD), cognitive function disorder caused by chronic fatigue syndrome, etc., although not being limited thereto. The term is used in the broadest concept, including any cognitive function disorder that can be caused by various causes.

In an aspect, the present disclosure may relate to a method for improving cognitive function, which includes administering a ginseng fruit extract to a subject in need of cognitive function improvement.

In an aspect, the present disclosure may relate to use of a ginseng fruit extract for improving cognitive function.

In an aspect, the present disclosure may relate to a ginseng fruit extract for use in improving cognitive function.

In an aspect, the present disclosure may relate to a composition for improving, treating or preventing chronic fatigue syndrome, or for improving the symptoms of chronic fatigue syndrome, which contains a ginseng fruit extract as an active ingredient. Specifically, the composition for improving, treating or preventing chronic fatigue syndrome may be a pharmaceutical composition.

In an aspect, the present disclosure may relate to a composition for improving or preventing chronic fatigue syndrome, or for improving the symptoms of chronic fatigue syndrome, which contains a ginseng fruit extract as an active ingredient. Specifically, the composition for improving or preventing chronic fatigue syndrome may be a food composition.

In an aspect of the present disclosure, the symptoms of chronic fatigue syndrome may be one or more selected from a group consisting of decreased brain activity, reduced brain blood flow, cognitive function decline, disorder of the central nervous system, concentration deficit, attention deficit and memory deficit, depression, and decreased resistance to stresses.

In an aspect, the present disclosure may relate to a method improving, treating or preventing chronic fatigue syndrome, or for improving the symptoms of chronic fatigue syndrome, which includes administering a ginseng fruit extract to a subject in need of improvement, treatment or prevention of chronic fatigue syndrome or improvement of the symptoms of chronic fatigue syndrome.

In an aspect, the present disclosure may relate to a use of a ginseng fruit extract for improving, treating or preventing chronic fatigue syndrome, or for improving the symptoms of chronic fatigue syndrome.

In an aspect, the present disclosure may relate to a ginseng fruit extract for use in improving, treating or preventing chronic fatigue syndrome, or in improving the symptoms of chronic fatigue syndrome.

Ginsenoside Re which is contained in the ginseng fruit extract of the present disclosure in large quantities has a structure of Chemical Structure 1.

[Chemical Structure 1]

In an aspect of the present disclosure, the ginseng fruit extract may contain 5-30 wt %, specifically 7-20 wt %, of ginsenoside Re based on the total weight of the ginseng fruit extract. Specifically, the ginseng fruit extract may contain 0.1 wt % or more, 1 wt % or more, 5 wt % or more, 7 wt % or more, 10 wt % or more, 12.5 wt % or more, 13 wt % or more, 15 wt % or more, 17 wt % or more, 20 wt % or more or 23 wt % or more, and 25 wt % or less, 23 wt % or less, 20 wt % or less, 17 wt % or less, 15 wt % or less, 13 wt % or less, 12.5 wt % or less, 10 wt % or less, 7 wt % or less, 5 wt % or less or 1 wt % or less of ginsenoside Re based on the total weight of the ginseng fruit extract.

In an aspect of the present disclosure, the ginseng fruit extract may contain a protopanaxadiol-based ginsenoside (PD) and a protopanaxatriol-based ginsenoside (PT) at a weight ratio (PD/PT) of 0.1-1.5. Specifically, in an aspect of the present disclosure, the weight ratio (PD/PT) of the protopanaxadiol-based ginsenoside (PD) and the protopanaxatriol-based ginsenoside (PT) may be 0.1 or greater, 0.15 or greater, 0.2 or greater, 0.25 or greater, 0.3 or greater, 0.35 or greater, 0.4 or greater, 0.45 or greater, 0.5 or greater, 0.55 or greater, 0.6 or greater, 0.65 or greater, 0.69 or greater, 0.7 or greater, 0.73 or greater, 0.75 or greater, 0.8 or greater, 0.85 or greater, 0.9 or greater, 0.95 or greater or 1.0 or greater, and 1.5 or smaller, 1.3 or smaller, 1.0 or smaller, 0.95 or smaller, 0.9 or smaller, 0.85 or smaller, 0.8 or smaller, 0.75 or smaller, 0.73 or smaller, 0.7 or smaller, 0.69 or smaller, 0.65 or smaller, 0.6 or smaller, 0.55 or smaller, 0.5 or smaller, 0.45 or smaller, 0.4 or smaller, 0.3 or smaller, 0.2 or smaller or 0.1 or smaller. Specifically, in an aspect of the present disclosure, the weight ratio (PD/PT) of the protopanaxadiol-based ginsenoside (PD) and the protopanaxatriol-based ginsenoside (PT) may be 0.69 or 0.73.

In an aspect of the present disclosure, the ginseng fruit extract may be contained in an amount of 0.01-100 wt % based on the total weight of the composition. In an aspect of the present disclosure, the ginseng fruit extract may be contained in an amount of 0.01 wt % or more, 0.1 wt % or more, 1 wt % or more, 5 wt % or more, 10 wt % or more, 20 wt % or more, 30 wt % or more, 40 wt % or more, 50 wt % or more, 60 wt % or more, 70 wt % or more, 80 wt % or more, 90 wt % or more or 99 wt % or more, and 100 wt % or less based on the total weight of the composition.

In an aspect of the present disclosure, the ginseng fruit extract may contain 20 wt % or more of a crude saponin based on the total weight of the ginseng fruit extract. Specifically, in an aspect of the present disclosure, the ginseng fruit extract may contain 20 wt % or more, 22 wt % or more, 24 wt % or more, 26 wt % or more, 28 wt % or more, 30 wt % or more, 31 wt % or more, 32 wt % or more, 33 wt % or more, 35 wt % or more, 37 wt % or more, 40 wt % or more or 45 wt % or more, and 50 wt % or less, 46 wt % or less, 44 wt % or less, 42 wt % or less, 40 wt % or less, 38 wt % or less, 36 wt % or less, 34 wt % or less, 32 wt % or less, 30 wt % or less, 28 wt % or less, 26 wt % or less or 24 wt % or less of a crude saponin based on the total weight of the ginseng fruit extract.

In an aspect of the present disclosure, the ginseng fruit extract may be an extract of water or a $C_1$-$C_6$ lower alcohol. Specifically, in an aspect of the present disclosure, the $C_1$-$C_6$ lower alcohol may be one or more selected from a group consisting of methanol, alcohol, acetone, ether, ethyl acetate, diethyl ether, methyl ethyl ketone and chloroform, although not being limited thereto.

In an aspect of the present disclosure, the ginseng fruit extract may be an extract of a ginseng fruit crude saponin. Specifically, in an aspect of the present disclosure, the ginseng fruit crude saponin extract may be one obtained by extracting with an organic solvent after removing oil-soluble components from the ginseng fruit extract. More specifically, the organic solvent may be an organic solvent with low polarity. For example, it may be hexane, methylene chloride, ethyl acetate or butanol. Accordingly, in an aspect of the present disclosure, the ginseng fruit crude saponin extract may be a water-soluble fraction of an extract extracted with the organic solvent with low polarity.

In an aspect of the present disclosure, the composition may be in a form selected from a group consisting of a dust, a granule, a tablet, a soft or hard capsule and a drink, although not being limited thereto.

In the present disclosure, the "extract" incudes any substance obtained by extracting from a natural product regardless of the extraction method, extraction solvent, extracted ingredients or the type of the extract. The term is used in a broad concept, including any substance obtained by processing or treating the substance extracted from the natural product otherwise. Specifically, the processing or treatment may be fermenting or enzymatically treating the extract. Accordingly, in the present disclosure, the term extract is used in a broad concept, including a fermentation product, a concentration product or a drying product. Specifically, in the present disclosure, the extract may be a fermentation product.

In the present disclosure, the "ginseng fruit extract" incudes any substance obtained by extracting from a ginseng fruit regardless of the extraction method, extraction solvent, extracted ingredients or the type of the extract. The term is used in a broad concept, including a substance obtained by extracting by treating with heat, an acid, a base, an enzyme, etc. and any substance obtained by processing or treating the substance extracted from the ginseng fruit otherwise. Specifically, the processing or treatment may be fermenting or enzymatically treating the ginseng fruit extract. Accordingly, the ginseng fruit extract of the present disclosure may be a fermentation product. Also, in the present disclosure, the ginseng fruit extract may be an extract of a ginseng fruit described below. Specifically, it may be an extract of a live ginseng fruit or an extract of a dried ginseng fruit. In the present disclosure, a live ginseng fruit, a dried ginseng fruit or other processed products of a ginseng fruit that can be used for the extraction (e.g., a fermentation product, a dried pulverization product, etc.) may have similar or identical compositions. Accordingly, the live ginseng fruit, the dried ginseng fruit or the other processed products of a ginseng fruit, which have similar or identical compositions, may exhibit the same effect or use of the ginseng fruit extract described in the present disclosure.

In an aspect of the present disclosure, the "ginseng fruit" may be an extract, a live ginseng fruit, a pulverization product of a ginseng fruit, a drying product of a ginseng fruit, a drying and pulverization product of a ginseng fruit, or a fermentation product of a ginseng fruit, although not being limited thereto. Also, the ginseng fruit used in the present disclosure is not limited as to how it is obtained and it may be either cultivated or purchased commercially. The ginseng fruit of the present disclosure needs not necessarily be dried and is not limited in its form as long as the active ingredients of the ginseng fruit can be extracted appropriately. In the present disclosure, the live ginseng fruit may be a harvested ginseng fruit per se, not being dried or processed otherwise.

In an aspect of the present disclosure, the ginseng fruit extract may be prepared by a preparation method including:

a step (1) of obtaining a ginseng fruit extract by extracting a ginseng fruit with water, an organic solvent or a combination thereof.

In an aspect of the present disclosure, the method may further include, after the step (1), a step (2) of concentrating the extract.

In an aspect of the present disclosure, the method may further include, after the step (2), a step (3) of removing oil-soluble components from the concentration product.

In an aspect of the present disclosure, the step (3) of the method may further include extracting with an organic solvent after removing the oil-soluble components.

In an aspect of the present disclosure, the method may further include, after the step (3), a step (4) of concentrating the product obtained in the step (3). Specifically, the product obtained in the step (3) may be a concentration product having the oil-soluble components removed or an extract obtained by extracting with an organic solvent after removing the oil-soluble components.

In an aspect of the present disclosure, the ginseng fruit extract may be prepared by a method including:

a step (i) of extracting a ginseng fruit with water, an organic solvent or a combination thereof; and a step (ii) of removing oil-soluble components from the extract.

In an aspect of the present disclosure, the method may further include, after the step (ii), a step (iii) of extracting with an organic solvent after removing the oil-soluble components.

In an aspect of the present disclosure, the method may further include, after the step (iii), a step (iv) of concentrating the extract.

In an aspect of the present disclosure, the ginseng fruit extract may be prepared by a method including:

a step (a) of pretreating a ginseng fruit; and a step (b) of obtaining a ginseng fruit extract by extracting the pretreated ginseng fruit with water, an organic solvent or a combination thereof. Specifically, in an aspect of the present disclosure, the pretreatment may be drying the ginseng fruit. The drying method is not limited as long as it can be used to dry a plant fruit such as a ginseng fruit and is obvious to those skilled in the art. Specifically, in an aspect of the present disclosure, the drying may be sunlight drying, hot air drying, evaporation drying, spray drying or freeze-drying, more specifically, sunlight drying or hot air drying. More specifically, in an aspect of the present disclosure, the pretreatment may include: a step of separating and removing seeds from the ginseng fruit; and a step of drying the pulp and rind of the ginseng fruit.

In an aspect of the present disclosure, the method may further include, after the step (b), a step (c) of obtaining a ginseng fruit extract by concentrating the extract.

In an aspect of the present disclosure, the concentration may be concentration under reduced pressure. However, any method well known to those skilled in the art to which the present disclosure belongs may be used without limitation. Specifically, in an aspect of the present disclosure, the concentration may be concentration under reduced pressure, and the concentration under reduced pressure may be performed at 40-45° C.

In an aspect of the present disclosure, the method may further include, after the step (c), a step (d) of removing oil-soluble components.

In an aspect of the present disclosure, the removal of oil-soluble components may be performed by dissolving the ginseng fruit extract in water, adding diethyl ether and then removing using a separatory funnel.

In an aspect of the present disclosure, the method may further include, after the step (d), a step (e) of extracting by adding an organic solvent after removing the oil-soluble components.

Specifically, in an aspect of the present disclosure, the step (e) may further include a step of extracting by adding an organic solvent and obtaining a ginseng fruit extract by concentrating the extract.

In an aspect of the present disclosure, the water may include distilled water or purified water and the organic solvent may include one or more selected from a group consisting of an alcohol, e.g., a $C_1$-$C_6$ lower alcohol, acetone, an ether, ethyl acetate, diethyl ether, methyl ethyl ketone, chloroform, hexane, methylene chloride, ethyl acetate and n-butanol, although not being limited thereto. Specifically, in an aspect of the present disclosure, the organic solvent used to extract the ginseng fruit may be water, ethanol or a combination thereof. And, the organic solvent used to remove the oil-soluble components may be an organic solvent with lower polarity than the organic solvent used to extract the ginseng fruit. For example, n-butanol may be used.

In an aspect of the present disclosure, the extraction may be performed, for example, by hot water extraction, heating extraction, cold precipitation extraction, reflux extraction, reflux condensation extraction, ultrasonic extraction, etc. However, any extraction method obvious to those skilled in the art may be used without limitation. Although the extraction may be performed at room temperature, it may be performed under a heating condition for more effective extraction. Specifically, the extraction may be performed at about 40-100° C., more specifically at about 80° C., although not being limited thereto. Extraction time may be specifically about 2-4 hours, more specifically about 3 hours, although not being limited thereto. The extraction time may be varied depending on the conditions such as the extraction solvent, the extraction temperature, etc. Specifically, when the solvent is water, the extraction may be performed at 90-100° C., and when the solvent is ethanol, the extraction may be performed at 65-70° C. The extraction may be performed more than once to obtain the active ingredient in large quantities. Specifically, the extraction may be performed continuously for 1-5 times, more specifically for 3 times. Specifically, in an aspect of the present disclosure, the extraction may be reflux extraction and may be performed at room temperature.

In an aspect of the present disclosure, the ginseng fruit extract may be prepared by reflux extracting the ginseng fruit at room temperature using water or an organic solvent and then concentrating under reduced pressure. The organic solvent may be ethanol.

Specifically for example, in an aspect of the present disclosure, the ginseng fruit extract may be prepared by a method including: a step of preparing a crude ginseng fruit by removing seeds from a live ginseng fruit and hot air drying the pulp and rind of the ginseng fruit; and a step of reflux extracting 500 g to 1.5 kg of the crude ginseng fruit at room temperature by adding 2-4 L of water or an alcohol (ethanol), filtering and then concentrating under reduced pressure at 40-45° C., although not being limited thereto.

The pharmaceutical composition according to the present disclosure may be in various oral or parenteral formulations. Specifically, the pharmaceutical composition according to the present disclosure may be provided in the form of an oral formulation. The formulation is prepared using a commonly used diluent or excipient such as a filler, an extender, a binder, a wetting agent, a disintegrant, a surfactant, etc. Solid formulations for oral administration include a tablet, a pill, a dust, a granule, a soft or hard capsule, etc. These solid formulations are prepared by mixing one or more active ingredient with at least one excipient such as starch, calcium carbonate, sucrose, lactose, gelatin, etc. In addition to the simple excipient, lubricants such as magnesium stearate, talc, etc. are also used. Liquid formulations for oral administration include a suspension, a liquid for internal use, an emulsion, a syrup, etc. In addition to a commonly used simple diluent such as water and liquid paraffin, various excipients such as a wetting agent, a sweetener, an aromatic, a preservative, etc. may be included. Formulations for parenteral administration include a sterile aqueous solution, a non-aqueous solution, a suspension, an emulsion, a lyophilized preparation and a suppository. The non-aqueous solution or suspension may use propylene glycol, polyethylene glycol, vegetable oil such as olive oil, an injectable ester such as ethyl oleate, or the like. As a base of the suppository, witepsol, macrogol, tween 61, cocoa butter, laurin butter, glycerogelatin, etc. may be used.

For pharmaceutical administration, the composition according to the present disclosure may be used in the form of a pharmaceutically acceptable salt and it may be used either alone or in combination with another pharmaceutically active compound. The salt is not particularly limited as long as it is pharmaceutically acceptable. For example, hydrochloride, sulfate, nitrate, phosphate, hydrofluoride, hydrobromide, formate, acetate, tartrate, lactate, citrate, fumarate, maleate, succinate, methanesulfonate, benzenesulfonate, toluenesulfonate, naphthalenesulfonate, etc. may be used.

The composition according to the present disclosure may be administered parenterally or orally depending on purposes, with a daily dosage of 0.1-500 mg, specifically 1-100 mg, per kg of body weight. The administration can be made once or several times a day. The administration dosage for a particular patient may vary depending on the body weight, age, sex and health condition of the patient, diet, administration time, administration method, excretion rate, severity of disease, or the like.

The pharmaceutical composition according to the present disclosure may be prepared into any suitable formulation including an oral formulation such as a dust, a granule, a tablet, a soft or hard capsule, a suspension, an emulsion, a syrup, a drink, an aerosol, etc. and a pharmaceutical formulation such as a formulation for external application to skin such as an ointment, a cream, etc., a suppository, an injection, a sterile solution for injection, etc. according to commonly employed methods.

The composition according to the present disclosure may be administered to a mammal such as rat, mouse, livestock, human, etc. via various routes including parenteral and oral routes. Every mode of administration may be expected. For example, it may be administered orally, rectally, intravenously, intramuscularly, subcutaneously, intrauterinally or intracerebroventricularly.

In an aspect of the present disclosure, the food composition may be a health functional food composition.

The formulation of the food composition of the present disclosure is not particularly limited. For example, it may be formulated into a dust, a tablet, a granule, a powder, a soft or hard capsule, a liquid such as a drink, a caramel, a gel, a bar, etc. For each formulation of the food composition, those skilled in the art may adequately select and add the ingredients commonly used in the art in addition to the active ingredient considering the particular formulation or purpose of use. A synergic effect may be achieved when different ingredients are used together.

In the food composition of the present disclosure, determination of the administration dosage of the active ingredient is within the level of those skilled in the art. A daily administration dosage may be, for example, 0.1-5000 mg/kg/day, more specifically 50-500 mg/kg/day, although not being limited thereto. The administration dosage may vary depending on various factors, including the age and health condition of the subject, the presence of complication(s), etc.

The food composition of the present disclosure may be, for example, various foods such as chewing gums, caramels, candies, frozen dessert, confectionery, etc., various drinks such as carbonated drinks, mineral water, alcoholic beverages, etc., or health functional foods including vitamins, minerals, etc.

In addition, the food composition according to an aspect of the present disclosure may contain various nutrients, vitamins, minerals (electrolytes), flavors including synthetic and natural flavors, colorants, extenders (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated drinks, etc. In addition, the functional food composition of the present disclosure may contain pulp for preparing natural fruit juice, fruit juice and vegetable juice. These ingredients may be used independently or in combination. The addition amount of these additives is no significant importance. In generable, they may be added within a range of about 20-100 parts by weight per 100 parts by weight of the composition according to the present disclosure.

Hereinafter, the present disclosure will be described in detail through examples. However, the technical scope of the present disclosure is not limited by the examples.

EXAMPLE 1

Preparation of Ginseng Fruit Extract

1) Pretreatment of ginseng fruit: The fruit of live ginseng (*Panax ginseng* C. A. Meyer) was harvested. After separating and removing seeds, a crude ginseng fruit was prepared by sunlight drying or hot air drying the pulp and rind of the ginseng fruit.

2) Preparation of ginseng fruit extract: 3 L of ethanol was added to 1 kg of the crude ginseng fruit. After reflux extracting at 70° C. for 4 hours and then filtering, 300 g of a ginseng fruit extract was obtained by concentrating under reduced pressure at 45° C.

EXAMPLE 2

Preparation of Live Ginseng Fruit Extract

The fruit of live ginseng (*Panax ginseng* C. A. Meyer) was harvested. After separating and removing seeds, a crude ginseng fruit was prepared by mixing the juice, pulp and rind of the ginseng fruit. 3 L of ethanol was added to 1 kg of the crude ginseng fruit. After reflux extracting at 70° C. for 4 hours and then filtering, 30 g of a ginseng fruit extract was obtained by concentrating under reduced pressure at 45° C.

COMPARATIVE EXAMPLE 1

Preparation of Ginseng Root Extract 300 g of a ginseng root extract was prepared in the same manner as in Example 1, except for using a ginseng root instead of the ginseng fruit.

TEST EXAMPLE 1

Comparison of Components of Ginseng Fruit and Ginseng Root Extracts

1. Analysis of Ginsenoside (Ginseng Saponin) Components of Ginseng Fruit and Ginseng Root The ginseng fruit extracts and the ginseng root extract prepared in Example 1, Example 2 and Comparative Example 1 were treated with ether to remove oil-soluble components. After extracting a crude saponin using butanol (BuOH) and concentrating, the ginsenoside components were analyzed by HPLC. The result is shown in FIG. 1 and Table 1.

TABLE 1

|  | Example 1 | Example 2 | Comparative Example 1 |
| --- | --- | --- | --- |
| Crude saponin content (dry weight) | 33.42% | 31.08% | 16.70% |
| PD/PT ratio | 0.73 | 0.69 | 3.23 |

Figure 1:
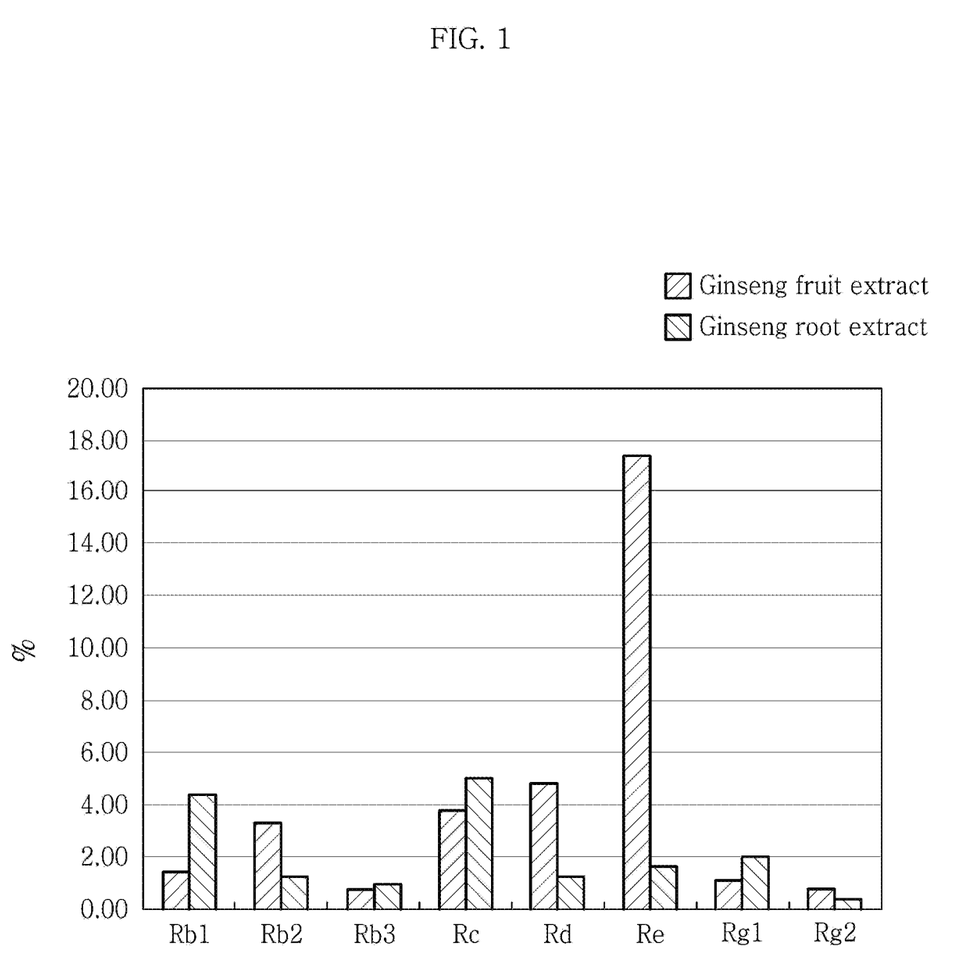
FIG. 1 shows a result of analyzing the ginsenoside components of a ginseng fruit extract and a ginseng root extract.

From FIG. 1 and Table 1, it can be seen that the ginseng fruit extracts prepared in Example 1 and Example 2 contain about 2 times of crude saponin as compared to the ginseng root extract prepared in Comparative Example 1. It can be also seen that the ginseng fruit extracts and the ginseng root extract show distinct difference in the ratio of the PD (protopanaxadiol)-based ginsenosides Rb1, Rb2, Rc and Rd to the PT (protopanaxatriol)-based ginsenosides Re, Rg1 and Rg2 as 0.73, 0.69 and 3.23, respectively.

2. Analysis of Mineral Components of Ginseng Fruit Extract

To confirm the characteristics of the ginseng fruit extracts prepared in Example 1 and Example 2 as "fruit" distinguished from ginseng, the vitamin and mineral components were analyzed. The result is shown in Table 2.

TABLE 2

| Components | Example 1 | Example 2 | Components | Example 1 | Example 2 |
| --- | --- | --- | --- | --- | --- |
| Potassium (mg/100 g) | 5865.57 | 4977.50 | Magnesium (mg/100 g) | 354.38 | 297.54 |
| Calcium (mg/100 g) | 819.26 | 914.22 | Zinc (mg/100 g) | 178.49 | 201.25 |
| Iron (mg/100 g) | 59.31 | 52.11 | Vit. A (µg/100 g, RE) | 213.11 | 145.85 |
| Phosphorus (mg/100 g) | 187.17 | 156.95 | Vit. $B_1$ (mg/100 g) | 12.29 | 10.09 |
| Vit. $B_2$ (mg/100 g) | 8.45 | 5.05 | Vit. $B_6$ (mg/100 g) | 10.50 | 15.44 |
| Vit. C (mg/100 g) | 4.91 | 7.13 | Vit. E (mg/100 g, α-TE) | 23.61 | 31.25 |
| Vit. K (µg/100 g) | 232.12 | 129.82 | Niacin (mg/100 g, NE) | 5.76 | 2.01 |
| Pantothenic acid (mg/100 g) | 5.87 | 6.15 | Folic acid (µg/100 g) | 349.97 | 423.35 |

As can be seen from above, the ginseng fruit used in the present disclosure contain more ginseng saponins than the ginseng root and their composition is quite different. Also, the ginseng fruit is rich in the 16 vitamin and mineral components as compared to the ginseng root. In addition, it can be seen that the extract obtained after drying the ginseng fruit and the extract obtained by extracting the live ginseng fruit per se are nearly the same in composition. Accordingly, the two extracts having similar compositions are expected to exhibit the same effect in the experiments described in the followings.

<Recruiting of Subjects of Normal Group and Test Group>

Experiment was conducted as follows to confirm the effect of the composition containing the ginseng fruit extract. Test Examples 2, 3 and 4 were conducted for a normal control group (normal group) and a test group.

The test group with chronic fatigue syndrome consisted of eight women patients in their 20s through 70s, who were diagnosed by a psychiatrist according to the criterion of the US CDC (Centers for Disease Control and Prevention) (Fukuda et al. 1994). The normal group consisted of eight women with similar ages to those of the test group, who had no axis I psychiatric disorders.

The subjects who had vision or hearing problems to the extent that testing was difficult, who could not receive magnetic resonance imaging, who had experienced head injury accompanied by loss of consciousness, who were suspected of axis I psychiatric disorder except mild depression symptoms, who were detected with signs of abnormality such as cerebral infarction, tumor, etc. in magnetic resonance imaging, and who had internal or neurological diseases that affect the brain function were excluded. After the subjects eligible for the study were selected according to these inclusion and exclusion criteria, experiment was conducted under consent.

The ginseng fruit extract prepared in Example 1 was mixed with water to prepare a 20-mL liquid formulation. The test group with chronic fatigue syndrome and the normal group were asked to drink the liquid formulation 20 mL a day, for 5 weeks.

The subjects made self-evaluation and were interviewed regarding the severity of chronic fatigue and depression before and after drinking the ginseng fruit extract. Also, the Stroop test was conducted and the brain blood flow was measured by functional magnetic resonance imaging (fMRI). After 5 weeks, the same tests were conducted and comparison was made before and after the intake.

TEST EXAMPLE 2

Self-evaluation of Severity of Chronic Fatigue and Depression

The severity of chronic fatigue and depression of the test group and the normal group subject was self-evaluated using questionnaires. The FibroFatigue Scale (Zachrisson et al., 2002) was used for the evaluation of the severity of chronic fatigue syndrome, and the Beck Depression Inventory (Beck et al., 1996) and the Beck Anxiety Inventory (Beck and Steer, 1990) were used for the evaluation of the severity of depression.

After the self-evaluation using questionnaires, the subjects were interviewed by a psychiatrist with population sociological variables. After the interview, the result was presented as scores. The result of comparing before and after the intake of the liquid formulation containing the ginseng fruit extract and the result of comparing before and after the intake for 5 weeks is shown in FIGS. 2 and 3.

Figure 2:
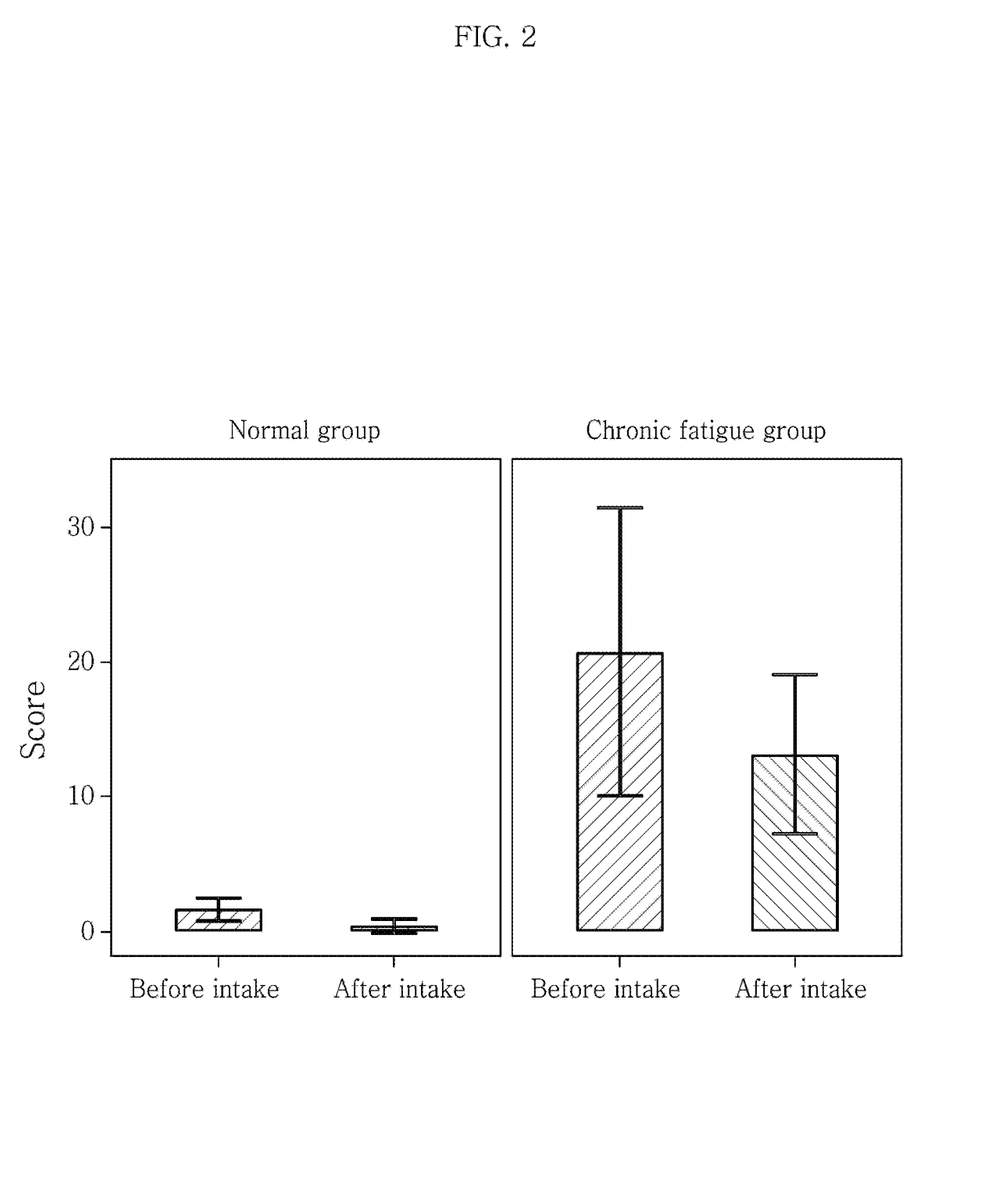
FIG. 2 shows a result of comparing improvement in depression of a normal control group and a test group before and after intake of a ginseng fruit extract.
Figure 3:
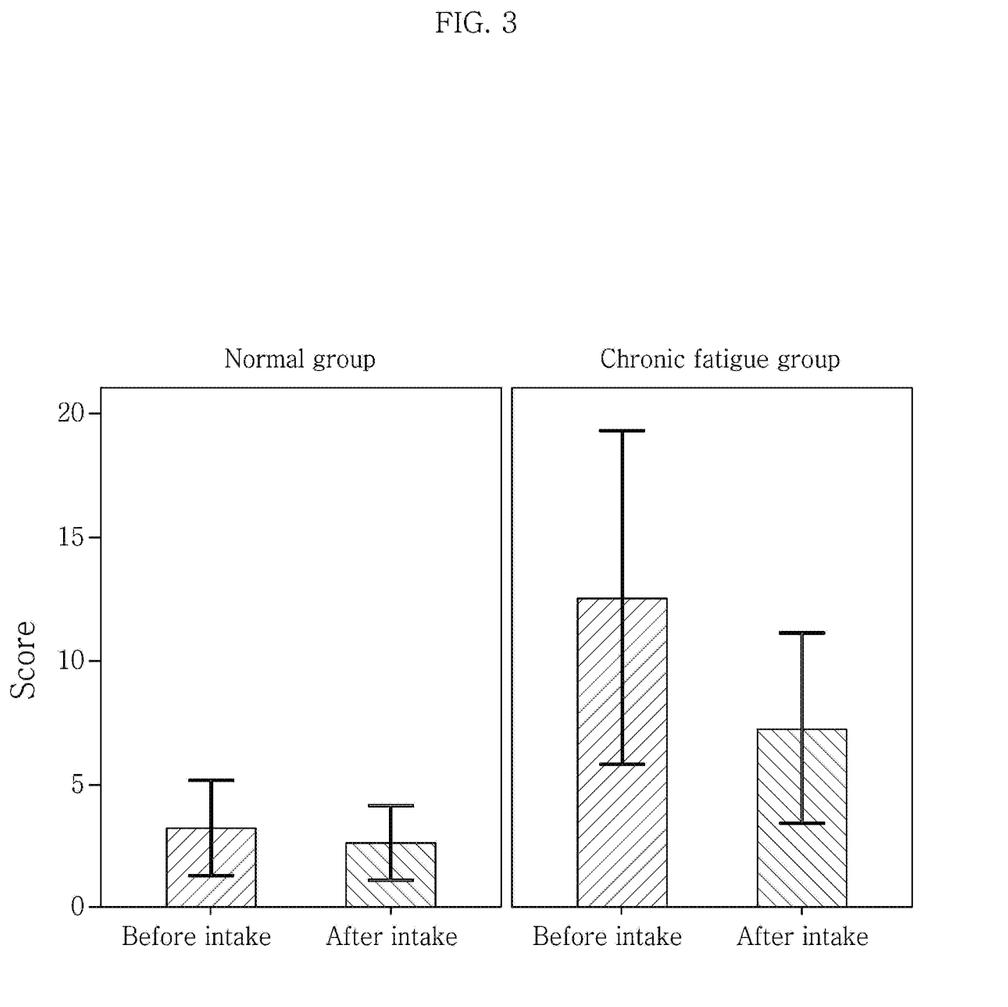
FIG. 3 shows a result of comparing improvement in chronic fatigue of a normal control group and a test group before and after intake of a ginseng fruit extract.

As seen from FIGS. 2 and 3, the chronic fatigue group had much higher fatigue scores than the normal group. The chronic fatigue group showed decrease in the severity of chronic fatigue and depression after the intake of the ginseng fruit extract. The severity of depression was improved by about 43% after the intake, and the severity of chronic fatigue was improved by about 40% after the intake.

Accordingly, it was confirmed that the ginseng fruit extract has superior effect of improving the severity of chronic fatigue and depression felt by humans.

TEST EXAMPLE 3

Stroop Test

For adequate reaction, efforts to suppress typical and automatic reactions are necessary. The Stroop test is a test wherein, when the word "Green" is written in red color, one should press a red button. It is a task requiring considerably controlled attention in a mismatching situation to suppress automatic reactions. Accordingly, by measuring accuracy and problem-solving time in the Stroop test, the information processing ability and the cognitive ability can be evaluated.

The Stroop test was conducted for the test group and the normal group before and after the intake of the ginseng fruit extract. For example, when the words 'Red (in yellow color), Blue (in red color) and Yellow (in blue color)' are written on one page, the test subject was supposed to name the colors in sequence, not the words. When pages of similar patterns are presented in sequence, the cognitive and information processing abilities of the test subject are measured by evaluating how accurate and fast the test subject can give the right answer. The accuracy was calculated by counting the numbers of correct and incorrect answers and the response speed was determined by measuring the time until the test was completed.

Figure 4:
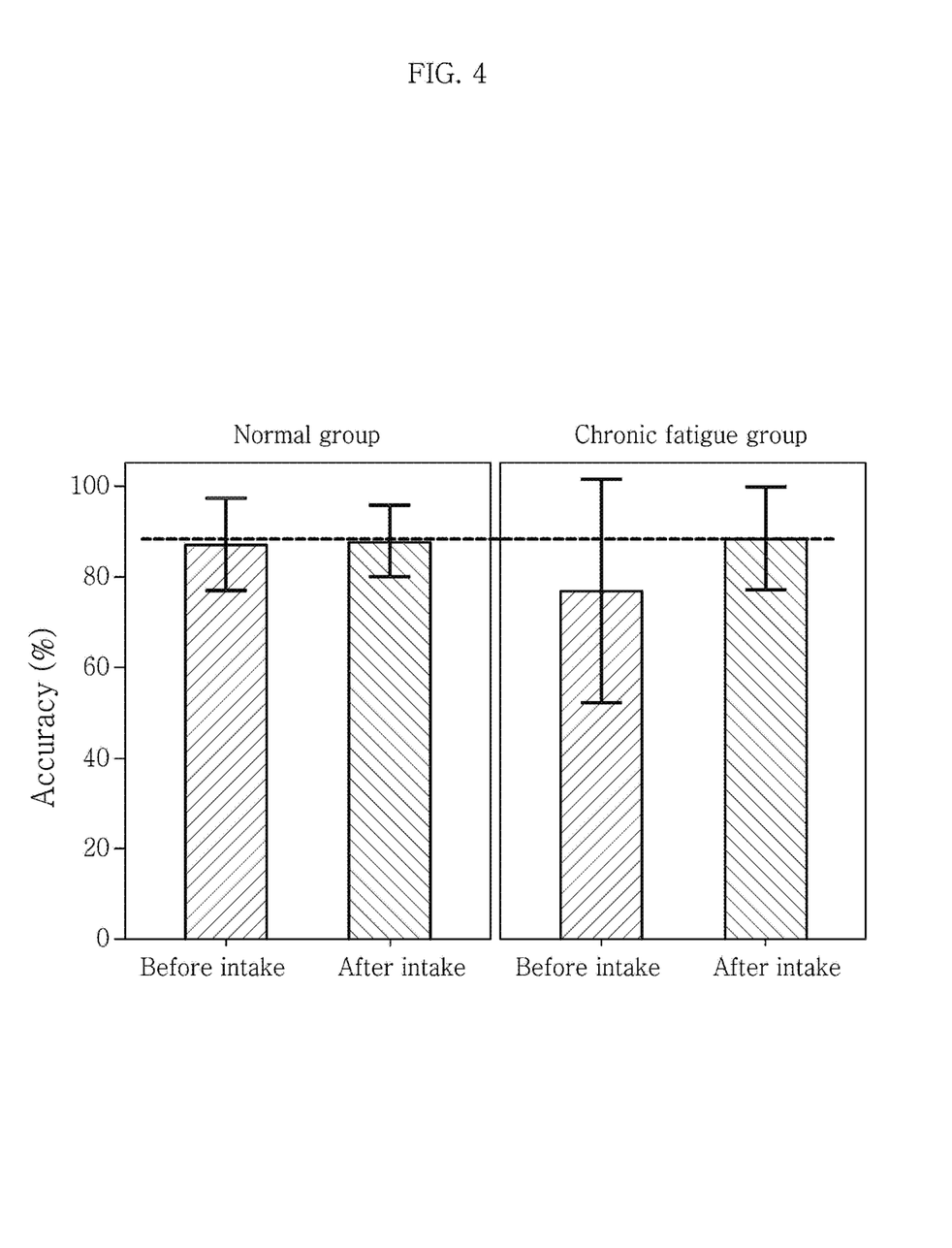
FIG. 4 shows a result of comparing improvement in accuracy in a Stroop test of a normal control group and a test group before and after intake of a ginseng fruit extract.
Figure 5:
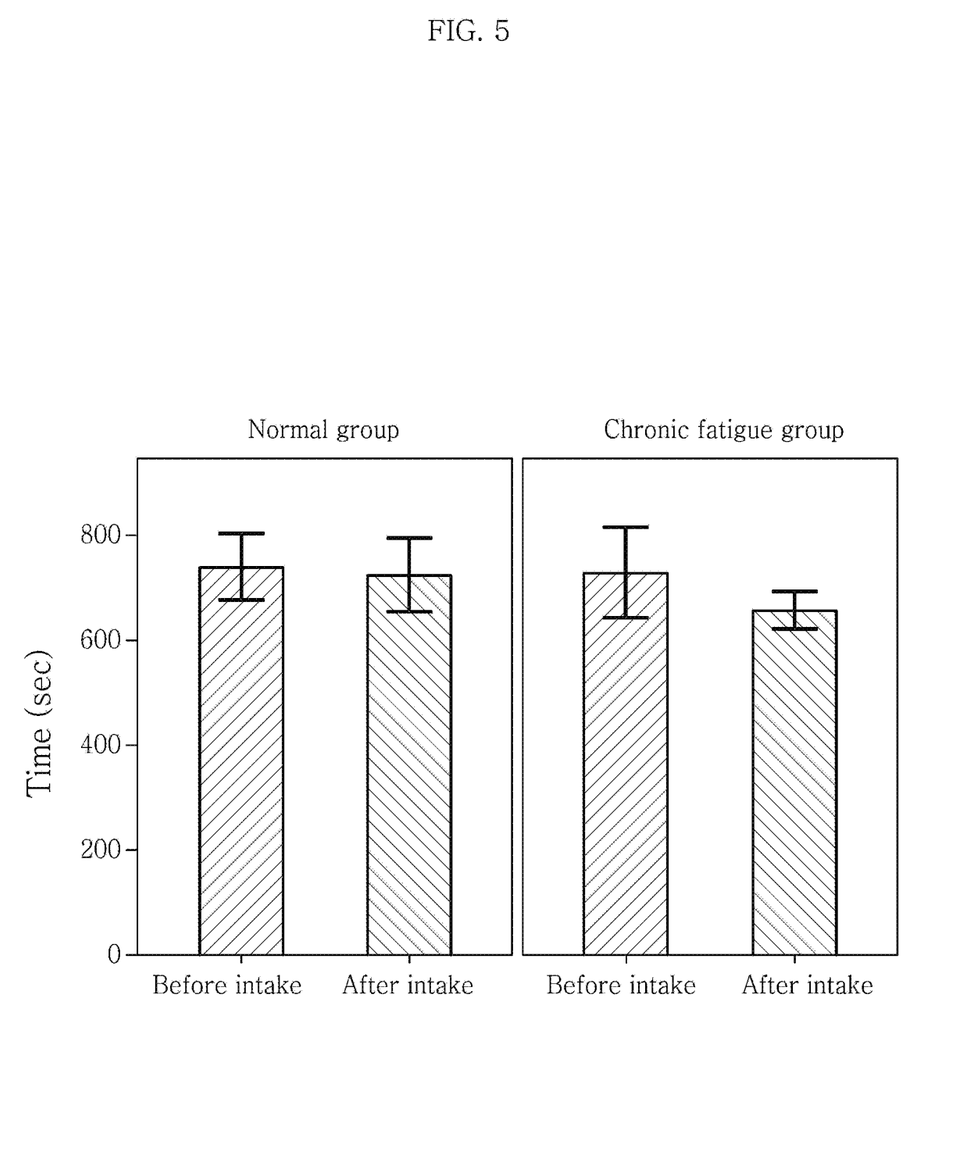
FIG. 5 shows a result of comparing improvement in response speed in a Stroop test of a normal control group and a test group before and after intake of a ginseng fruit extract.

As seen from FIGS. 4 and 5, the chronic fatigue group showed lower accuracy than the normal group, but the accuracy was improved significantly after the intake of the ginseng fruit extract and the response speed was also improved significantly.

Accordingly, it was confirmed that the ginseng fruit extract has a superior effect of improving cognitive ability, as evidenced by the improvement in problem-solving accuracy and speed. This effect is thought to be due to the improved brain activity owing to increased brain blood flow as will be described below.

TEST EXAMPLE 4

Measurement of Brain Blood Flow by Functional Magnetic Resonance Imaging

Functional magnetic resonance imaging (fMRI) allows for imaging of the change of blow flood in different brain parts by scanning the brain in real time. The level of brain activation can be compared by representing the parts with more blood flow and less blood flow with different colors.

For the test group and the normal group, the activation and functional connectivity of the attention-related brain parts were investigated by fMRI before and after the intake of the ginseng fruit extract. And, their correlation with the Stroop test result was analyzed.

fMRI was conducted using the 3.0T MRI instrument (Siemens). BOLD (blood oxygen level-dependent) signals were imaged with a gradient-echo EPI sequence along the axial direction. A head restraint was used to avoid image distortion caused by the movement of the subject, and earplugs were used to mitigate mechanical noise.

Figure 6A:
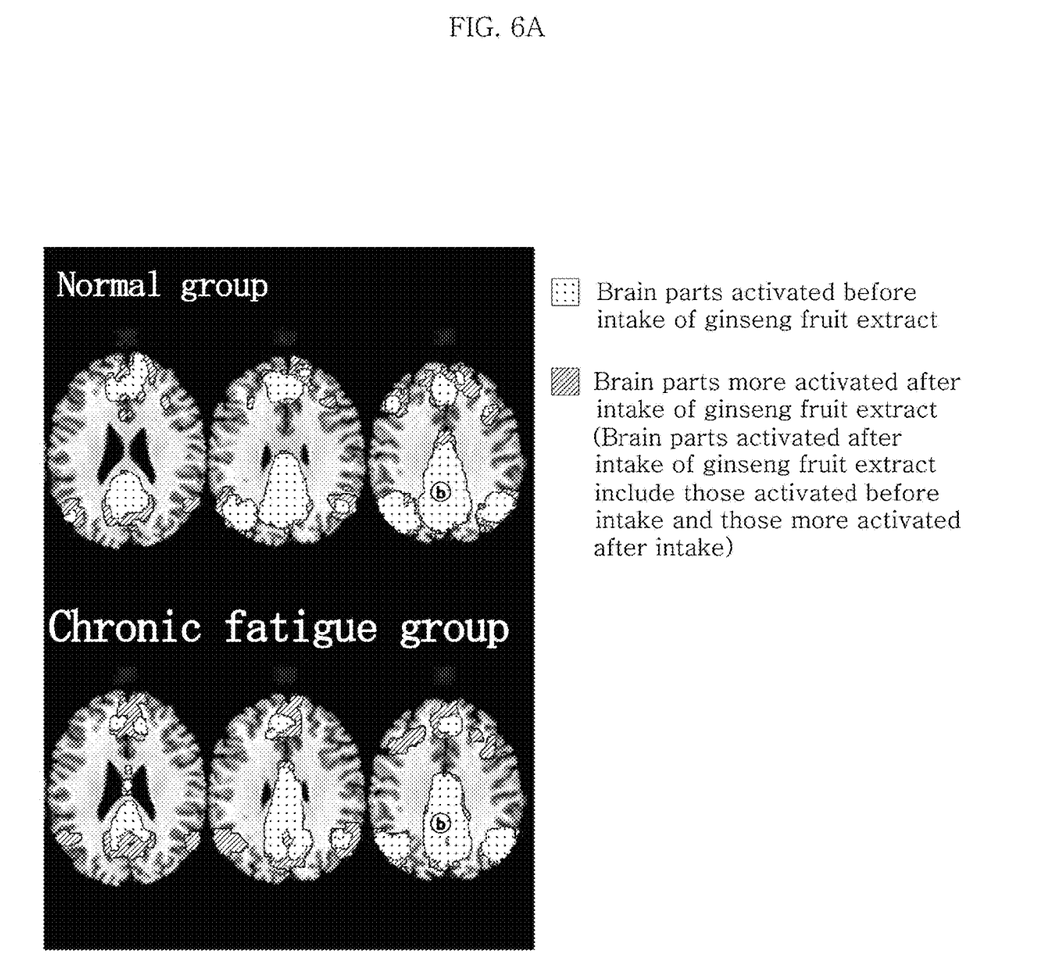
FIG. 6a shows a result of comparing brain blood flow of a normal control group and a test group before and after intake of a ginseng fruit extract measured by functional magnetic resonance imaging.
Figure 6B:
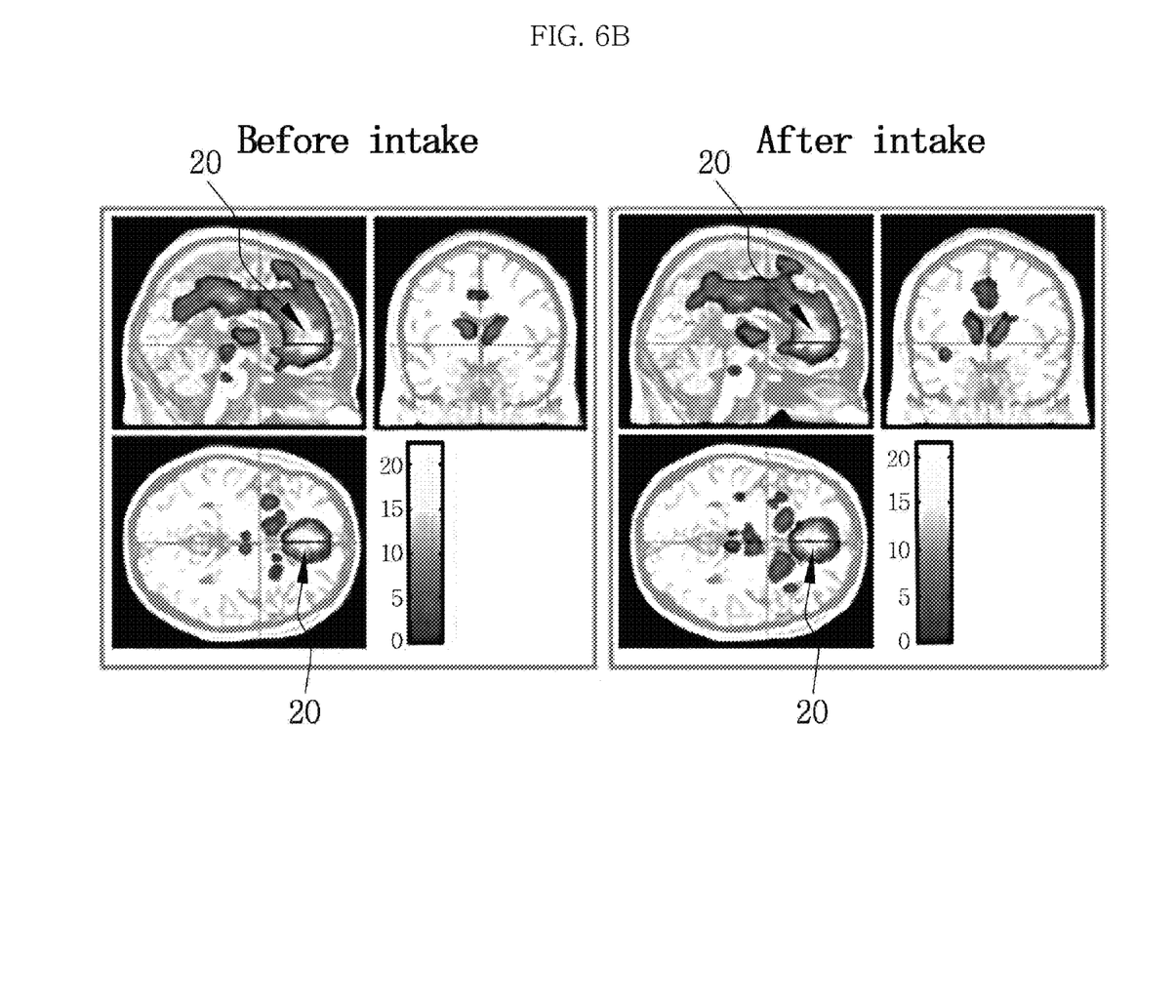
FIG. 6b shows a result of further comparing brain blood flow of a test group before and after intake of a ginseng fruit extract measured by functional magnetic resonance imaging. In the figure, the region 20 indicated by the arrow is the region where the brain activity is the highest. The darker regions are the regions where the activity is lower.

The fMRI images of the test group and the normal group before and after the intake of the ginseng fruit extract were compared. The fMRI images of the test group and the normal group before and after the intake are shown in FIGS. 6a and 6b. The parts that were activated before the intake of the ginseng fruit extract are represented as dotted regions, and the parts that were more activated after the intake are represented as dashed regions (FIG. 6a). In FIG. 6a, the dashed regions are the parts which were more activated as compared to before the intake, and the whole parts that were activated after the intake of the ginseng fruit extract include the dotted regions and the dashed regions.

The test group which showed difference before and after the intake was further analyzed (FIG. 6b). In the figure, the brightest region indicated by the arrow is the region where the brain activity is the highest, and the darker regions are the regions where the activity is lower.

As seen from FIG. 6a, for the normal group, there were few dashed regions and most of the activated parts were dotted regions, indicating that, although the activated regions slightly increased after the intake of the ginseng fruit extract, there was no significant difference before and after the intake.

But, for the test group, the dashed regions increased significantly, indicating that the activated brain regions were significantly increased after the intake. In particular, the dashed regions increased in the frontal lobe and the occipital lobe.

In addition, as can be seen from FIG. 6b, the brain sectional images taken from the side revealed that the activity of the part connecting the frontal lobe and the occipital lobe increased. And, the brain sectional images taken from the front show that the activity of the part penetrating the frontal lobe and the occipital lobe increased significantly. In addition, the brain sectional images taken from above also show that the activity of the part in front of the occipital lobe was increased. These results suggest that the brain connectivity was improved due to the increased connectivity strength between the frontal lobe and the occipital lobe of the brain.

Accordingly, it is thought that the increase in the activated parts of the brain and the increase in the connectivity strength between the frontal lobe and the occipital lobe lead to the improved problem-solving accuracy and speed in cognitive ability as demonstrated by the Stroop test.

Hereinafter, formulation examples of the composition according to an aspect of the present disclosure will be described. However, they are for illustrative purposes only and the scope of the present disclosure is not limited by the formulation examples.

FORMULATION EXAMPLE 1

Soft Capsule

A soft capsule filling solution was prepared by mixing 8 mg of the ginseng fruit extract of Example 1 or Example 2, 9 mg of vitamin E, 9 mg of vitamin C, 2 mg of palm oil, 8 mg of hydrogenated vegetable oil, 4 mg of yellow beeswax and 9 mg of lecithin and filled in a soft capsule, with 400 mg per capsule. Separately from this, a soft capsule sheet was prepared using 66 parts by weight of gelatin, 24 parts by weight of glycerin and 10 parts by weight of a sorbitol solution and was filled with the filling solution to prepare a soft capsule containing 400 mg of the ginseng fruit extract according to the present disclosure.

FORMULATION EXAMPLE 2

Tablet 8 mg of the ginseng fruit extract of Example 1 or Example 2, 9 mg of vitamin E, 9 mg of vitamin C, 200 mg of galactooligosaccharide, 60 mg of lactose and 140 mg of maltose were mixed and granulated using a fluidized bed dryer. After adding 6 mg of sugar ester, 500 mg of the resulting composition was prepared into a tablet according to a commonly employed method.

FORMULATION EXAMPLE 3

Drink 8 mg of the ginseng fruit extract of Example 1 or Example 2, 9 mg of vitamin E, 9 mg of vitamin C, 10 g of glucose, 0.6 g of citric acid and 25 g of oligosaccharide syrup were mixed and 300 mL of purified water was added. 200 mL of the resulting mixture was filled per bottle and sterilized at 130° C. for 4-5 seconds.

FORMULATION EXAMPLE 4

Granule 8 mg of the ginseng fruit extract of Example 1 or Example 2, 9 mg of vitamin E, 9 mg of vitamin C, 250 mg of anhydrous crystalline glucose and 550 mg of starch were mixed and formed into granules using a fluidized bed granulator. The granules were filled in a pouch.

FORMULATION EXAMPLE 5

Injection

An injection was prepared with the composition described in Table 3 according to a commonly employed method.

TABLE 3

| Ingredients | Contents |
| --- | --- |
| Ginseng fruit extract of Example 1 or Example 2 | 10-50 mg |
| Sterile distilled water for injection | adequate |
| pH control agent | adequate |

FORMULATION EXAMPLE 6

Health Functional Food

A health functional food was prepared with the composition described in Table 4 according to a commonly employed method.

TABLE 4

| Ingredients | Contents |
| --- | --- |
| Ginseng fruit extract of Example 1 or Example 2 | 20 mg |
| Vitamin A acetate | 70 µg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 µg |
| Vitamin C | 10 mg |
| Biotin | 10 µg |
| Nicotinamide | 1.7 mg |
| Folic acid | 50 µg |
| Calcium pantothenate | 0.5 mg |
| Ferrous sulfate | 1.75 mg |
| Zinc oxide | 0.82 mg |
| Magnesium carbonate | 25.3 mg |
| Potassium dihydrogen phosphate | 15 mg |
| Calcium monohydrogen phosphate | 55 mg |
| Potassium citrate | 90 mg |
| Calcium carbonate | 100 mg |
| Magnesium chloride | 24.8 mg |

The compositional ratios of the vitamin and mineral mixtures are described as a specific example suitable for a health functional food but may be varied otherwise as desired.

FORMULATION EXAMPLE 7

Health Drink

A health drink was prepared with the composition described in Table 5 according to a commonly employed method.

TABLE 5

| Ingredients | Contents |
| --- | --- |
| Ginseng fruit extract of Example 1 or Example 2 | 1000 mg |
| Citric acid | 1000 mg |
| Oligosaccharide | 100 g |
| Taurine | 1 g |
| Purified water | balance |

The above ingredients were mixed and heated at 85° C. for about 1 hour while stirring according to a commonly employed method for preparing a health drink. The resulting solution was filtered and sterilized.

The invention claimed is:

1. A method for activating the brain or for improving cognitive function comprising: administering a ginseng fruit extract to activate the brain, to improve cognitive function to a subject having cognitive function disorders thereof,
    wherein the brain is activated or improves cognitive function in a subject in need, wherein the administration is administrating the effective amount of a ginseng fruit extract orally to a subject in need, and
    wherein the ginseng fruit extract is an ethanol extract of the ginseng fruit which is prepared by adding ethanol to a ginseng fruit, followed by refluxing and filtering, and then concentrating under reduced pressure, and comprises 30 wt % or more of a crude saponin based on the total weight of the ginseng fruit extract,
    wherein the cognitive function disorder is one or more selected from degenerative brain diseases, alcoholic cognitive function disorder, cognitive function disorder caused by cerebral hemorrhage, loss of brain function due to accidents, aging-induced cognitive function disorder, schizophrenia, and attention deficit hyperactivity disorder (ADHD).

2. The method according to claim 1, wherein the ginseng fruit extract comprises a protopanaxadiol-based ginsenoside (PD) and a protopanaxatriol-based ginsenoside (PT) at a weight ratio (PD/PT) of 0.1-1.5.

3. The method according to claim 1, wherein the ginseng fruit extract is comprised in a composition, wherein the ginseng fruit extract is comprised in an amount of 0.01-100 wt % based on the total weight of the composition.

4. The method according to claim 1, wherein the ginseng fruit extract comprises 5-30 wt % of ginsenoside Re based on the total weight of the ginseng fruit extract.

5. The method according to claim 1, wherein the composition is in a form selected from a group consisting of a dust, a granule, a tablet, a soft or hard capsule and a drink.

6. The method according to claim 1, wherein the activating the brain comprises increasing brain blood flow.

* * * * *